(12) United States Patent
Hamada et al.

(10) Patent No.: US 8,912,306 B2
(45) Date of Patent: Dec. 16, 2014

(54) HALOGEN-TERMINATED SULFER-CONTAINING POLYMER

(75) Inventors: Yukiko Hamada, Ichihara (JP);
Yasukazu Suga, Nagoya (JP); Koki Echigoya, Moriyama (JP); Kazunori Matsumoto, Cangzhou (CN); Tomohiro Oba, Ichihara (JP)

(73) Assignee: Toray Fine Chemicals Co., Ltd. (JP)

( * ) Notice: Subject to any disclaimer, the term of this patent is extended or adjusted under 35 U.S.C. 154(b) by 0 days.

(21) Appl. No.: 14/235,536

(22) PCT Filed: Jul. 6, 2012

(86) PCT No.: PCT/JP2012/067286
§ 371 (c)(1),
(2), (4) Date: Feb. 24, 2014

(87) PCT Pub. No.: WO2013/018501
PCT Pub. Date: Feb. 7, 2013

(65) Prior Publication Data
US 2014/0163150 A1     Jun. 12, 2014

(30) Foreign Application Priority Data
Jul. 29, 2011   (JP) .................. 2011-167330

(51) Int. Cl.
| | | |
|---|---|---|
| C08L 81/04 | (2006.01) | |
| C07C 323/12 | (2006.01) | |
| C08G 75/14 | (2006.01) | |
| C08K 5/00 | (2006.01) | |
| C08K 5/372 | (2006.01) | |
| G02B 6/02 | (2006.01) | |

(52) U.S. Cl.
CPC ............ C08L 81/04 (2013.01); C07C 323/12 (2013.01); C08G 75/14 (2013.01); C08K 5/0016 (2013.01); C08K 5/372 (2013.01); G02B 6/02033 (2013.01)
USPC ............................................. 528/373; 568/21

(58) Field of Classification Search
USPC ........................................... 568/21; 528/373
See application file for complete search history.

(56) References Cited

U.S. PATENT DOCUMENTS

| | | | |
|---|---|---|---|
| 2,466,963 A | 4/1949 | Patrick et al. | |
| 2,728,748 A * | 12/1955 | Davis | 528/265 |
| 3,400,104 A * | 9/1968 | Liggett | 528/265 |
| 4,124,645 A | 11/1978 | Bertozzi et al. | |

FOREIGN PATENT DOCUMENTS

| | | |
|---|---|---|
| JP | 49-110799 | 10/1974 |
| JP | 2003-128645 | 5/2003 |
| JP | 2009-126836 | 6/2009 |

* cited by examiner

*Primary Examiner* — Shane Fang
(74) *Attorney, Agent, or Firm* — DLA Piper LLP (US)

(57) ABSTRACT

A halogen-terminated sulfur-containing polymer is represented by:

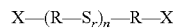

wherein R is an ether bond-containing alkyl group having 3 to 26 carbon atoms, X is a halogen atom, n is an integer of 1 to 200, and r has an average of 1 to 5.

10 Claims, No Drawings

HALOGEN-TERMINATED SULFER-CONTAINING POLYMER

TECHNICAL FIELD

This disclosure relates to a halogen-terminated sulfur-containing polymer. Specifically, the disclosure relates to a halogen-terminated sulfur-containing polymer usable as a plasticizer, an additive and an intermediate of a terminal modified sulfide polymer.

BACKGROUND

A conventional polysulfide polymer is produced by a method of obtaining a liquid polymer via a solid polymer by cleavage of polysulfide bond described in U.S. Pat. No. 2,466,963. Therefore, the terminal group of the liquid polymer is a thiol group. A thiol group-terminated liquid polysulfide polymer is easily oxidized by an oxidizing agent such as lead dioxide and manganese dioxide and cured. A cured rubbery material obtained by curing contains sulfur and does not contain a double bond in the main chain of the molecule. A cured material in which a liquid polymer is cured is characterized in excellent oil resistance, weather resistance, water tightness and gas tightness, and also good in adhesion, thus is widely used as a sealant, adhesive and paint.

Since the conventional polysulfide polymer has very high polarity, usable plasticizer is limited to plasticizers such as phthalic esters, chlorinated paraffins, dipropylene glycol dibenzoate and hydrogenated terphenyl and the like. However, BBP (butyl benzyl phthalate) is listed as a safety hazardous material in Europe (substance on the SVHC list under REACH regulation as of December 2010), and the future usage is possibly restricted. Manufacture and use of most of the plasticizers that can be used for a polysulfide polymer are being strictly restricted by the effect of tightening of regulations on chemical substances. Therefore, there is a growing need for the development of a new plasticizer for a polysulfide polymer.

Thus, there is a need to provide a new plasticizer for a polysulfide polyer having high compatibility with a polysulfide polymer.

SUMMARY

The halogen-terminated sulfur-containing polymer is a halogen-terminated sulfur-containing polymer represented by the following formula:

$$X-(R-S_r)_n-R-X$$

wherein R is an ether bond-containing alkyl group having 3 to 26 carbon atoms, X is a halogen atom, n is an integer of 1 to 200, and r has an average of 1 to 5.

The halogen-terminated sulfur-containing polymer easily mixes with a polysulfide polymer in an arbitrary proportion, reduces viscosity and exhibits plasticizing effects, and can thus be utilized as a plasticizer of a polysulfide polymer. The halogen-terminated sulfur-containing polymer has a low glass-transition temperature as compared to high polar phthalate ester plasticizers and chlorinated paraffin plasticizers conventionally used for a polysulfide polymer, thus improving low-temperature flexing when used as a compound such as a sealant. In addition, use of phthalate ester plasticizers is being restricted due to recent tightening of regulations on chemical substances. Based on the above, the halogen-terminated sulfur-containing polymer is industrially very useful as a plasticizer of a polysulfide polymer.

In addition, the halogen-terminated sulfur-containing polymer can be used as a plasticizer for thioether polymers known under the trade name "Permapol P-3" and the like and high polar resins such as vinyl chloride, and an additive for materials requiring a high refractive index such as an optical fiber.

The halogen-terminated sulfur-containing polymer can easily thiolate the terminal by reacting sodium hydrosulfide or the like, and is thus effective as an intermediate when manufacturing a thiol group-terminated polysulfide polymer, that is, a conventional polysulfide polymer. Furthermore, the halogen-terminated sulfur-containing polymer can easily synthesize a compound other than compounds having a thiol terminal by adding a compound that reacts with a halogen.

DETAILED DESCRIPTION

Hereinbelow, our polymers and methods will be described in detail.

The halogen-terminated sulfur-containing polymer is a halogen-terminated sulfur-containing polymer represented by the following formula:

$$X-(R-S_r)_n-R-X$$

R is an ether bond-containing alkyl group having 3 to 26 carbon atoms, and preferably an ether bond-containing alkyl group having 3 to 16 carbon atoms, or an ether bond-containing alkyl group having 3 to 16 carbon atoms containing a branched alkylene group.

R is preferably an alkyl group containing —O—CH$_2$—O— bond and more preferably an alkyl group containing —C$_2$H$_4$—O—CH$_2$—O—C$_2$H$_4$— bond. R is further preferably an alkyl group containing the following chemical structure —C$_2$H$_4$—O—CH$_2$—O—C$_2$H$_4$— in an amount of 50 mol % or more, and further more preferably an alkyl group containing the following chemical structure —C$_2$H$_4$—O—CH$_2$—O—C$_2$H$_4$— in an amount of 70 mol % or more.

The branched alkylene group is preferably a multifunctional component derived from a trihalo organic compound and more preferably a multifunctional component derived from a trichloro organic compound. The branched alkylene group is further preferably an alkylene group represented by

The amount of the branched alkylene group is preferably 0 to 10 mol % and more preferably 0 to 5 mol %, based on the number of moles of the ether bond. When exceeding 5 mol %, the degree of crosslinking may increase, thus the viscosity may increase.

In the halogen-terminated sulfur-containing polymer, X is a halogen atom. Preferred halogen atom is a chlorine atom, a bromine atom and an iodine atom, and more preferred halogen atom is a chlorine atom.

In the halogen-terminated sulfur-containing polymer, n is an integer of 1 to 200, and preferably, n is an integer of 1 to 50. When n exceeds 50, the viscosity may increase and plasticizing effects as a plasticizer may decrease, and the reactivity of thiolation as an intermediate of the thiol group-terminated polysulfide polymer may decrease. The halogen-terminated sulfur-containing polymer is preferably a liquid form at room temperature, and more preferably has a number average molecular weight of 500 to 10,000.

The halogen-terminated sulfur-containing polymer is preferably obtained by reacting sodium polysulfide with at least one alpha, omega dihalo organic compound and, optionally, at least one trihalo organic compound, in the presence of a phase transfer catalysts.

Preferred phase transfer catalyst is quaternary ammonium salts, phosphonium salts and crown ethers, and more preferred phase transfer catalyst is methyltributylammonium halides, tetrabutylammonium halides, tetraphenylphosphonium halides and 18-crown-6. Further preferred phase transfer catalyst is tetrabutylammonium chloride, tetrabutylammonium bromide, methyltributylammonium chloride and methyltributylammonium bromide. The preferred amount of the phase transfer catalyst is 0.0001 to 0.1 mol and more preferably 0.0002 to 0.02 mol, per 1 mol of an organic group of R constituting the halogen-terminated sulfur-containing polymer.

The sulfur content of r is determined by adjustment of sodium sulfide when starting the reaction and can be adjusted by mixing sodium monosulfide ($Na_2S$) and sodium polysulfide ($Na_2S_x$: x is 2 or more) in arbitrary proportion. As sources of sodium monosulfide and sodium polysulfide, those adjusted by any convenient method such as combinations of sodium hydrosulfide, sodium hydroxide and sulfur, can be used.

The halogen-terminated sulfur-containing polymer is useful as a plasticizer of a polysulfide polymer. Using the halogen-terminated sulfur-containing polymer as a plasticizer, a polysulfide polymer, a curing agent and other fillers are added, whereby a curable composition can be obtained. In addition, the halogen-terminated sulfur-containing polymer can be used for the purpose of a plasticizer for thioether polymers such as Permapol P-3 and the like and high polar resins such as vinyl chloride, and for the purpose of an additive for materials requiring a high refractive index such as an optical fiber.

The curable composition comprises a halogen-terminated sulfur-containing polymer, a polysulfide polymer and a curing agent. When the average of r of the halogen-terminated sulfur-containing polymer is less than 2, the curable composition has major effects of low glass-transition temperature and high thermal resistance.

The curable composition preferably contains 1 to 100 parts by weight of a halogen-terminated sulfur-containing polymer, based on 100 parts by weight of a polysulfide polymer.

In the curable composition, a substance that has been used as a curing agent of a conventional polysulfide polymer can be used as a curing agent. Specific examples of the curing agent include inorganic oxidizing agents, polyisocyanate compounds or diisocyanate compounds, organic peroxidants, organic oxidizing agents, epoxy resins, and the like.

The inorganic oxidizing agents include inorganic peroxides such as manganese dioxide, lead dioxide, zinc peroxide, calcium peroxide, iron dioxide, barium peroxide, tellurium dioxide, selenium dioxide, tin dioxide, trilead tetraoxide, strontium peroxide and lithium peroxide, inorganic oxides such as zinc oxide, iron (II) oxide, lead oxide, iron (III) oxide, antimony trioxide, magnesium oxide, cobalt oxide, calcium oxide, copper oxide and barium oxide, sodium chromate, potassium chromate, sodium dichromate, potassium dichromate, sodium perchlorate, sodium perborate, potassium permanganate, sodium percarbonate, and the like. Among them, manganese dioxide and lead dioxide are preferred, in particular, manganese dioxide is preferred.

The polyisocyanate compound includes polymethylene polyphenylene polyisocyanate (polymeric MDI), triphenylmethane triisocyanate, dimethyltriphenylmethane tetraisocyanate, biuret products using the diisocyanate compound described below, trimethylolpropane adducts, isocyanurate trimers, and the like.

The diisocyanate compound include aromatic diisocyanates like TDI (for example, 2,4-tolylene diisocyanate (2,4-TDI), 2,6-tolylene diisocyanate (2,6-TDI)), MDI (for example, 4,4'-diphenylmethane diisocyanate (4,4'-MDI), 2,4'-diphenylmethane diisocyanate (2,4'-MDI)), 1,4'-phenylene diisocyanate, xylylene diisocyanate (XDI), tetramethyl xylylene diisocyanate (TMXDI), tolidine diisocyanate (TODI) and 1,5-naphthalene diisocyanate (NDI), aliphatic diisocyanates such as ethylene diisocyanate, propylene diisocyanate, tetramethylene diisocyanate, hexamethylene diisocyanate (HDI), trimethyl hexamethylene diisocyanate (TM-HDI), lysine diisocyanate and norbornane diisocyanate (NBDI), trans-cyclohexane-1,4-diisocyanate, isophorone diisocyanate (IPDI), and carbodiimide-modified diisocyanates thereof, and the like. Two or more kinds of the isocyanate compounds may be used.

The organic peroxide includes hydroperoxides, dialkyl peroxides, peroxy ketals, peroxy esters, peroxy dicarbonates, diacyl peroxides, and the like. In particular, cumene hydroperoxide, p-menthane hydroperoxide, diisopropyl benzene hydroperoxide and t-butyl peroxy benzoate are particularly excellent in hardness development, thus are a preferred organic peroxide. Two or more kinds of the organic peroxides may be used.

The organic oxidizing agent includes nitrobenzene, dinitrobenzene, p-quinone dioxime, and the like.

The epoxy resin includes epoxy resins obtained by adding epichlorohydrin to a polyhydric phenol such as bisphenol A, bisphenol F, resorcinol, hydroquinone, pyrocatechol, 4,4-dihydroxybiphenyl or 1,5-hydroxy naphthalene, epoxy resins obtained by adding epichlorohydrin to a polyhydric alcohol such as ethylene glycol, propylene glycol or glycerin, epoxy resins obtained by adding epichlorohydrin to an aromatic dicarboxylic acid such as oxybenzoic acid or phthalic acid, and the like, and those that are a liquid form at room temperature are preferred. The amines may be those known as a normal curing agent for an epoxy resin and include aliphatic diamines such as ethylenediamine, trimethylene diamine, hexamethylene diamine and tetramethylene diamine, aliphatic tertiary amines such as N,N-dimethylpropylamine and N,N,N',N'-tetramethyl hexamethylene diamine, alicyclic tertiary amines such as N-methylpiperidine and N,N'-dimethyl piperazine, aromatic tertiary amines such as benzyldimethylamine, dimethylaminomethyl phenol and 2,4,6-tris(dimethylaminomethyl) phenol, and the like.

The curable composition may contain as a plasticizer, other than the halogen-terminated sulfur-containing polymer of the present invention, hydrocarbon plasticizers such as phthalic esters, chlorinated paraffins, dipropylene glycol dibenzoate, diethylene glycol dibenzoate, triethylene glycol dibenzoate, dipropylene glycol monobenzoate and hydrogenated terphenyl, and the like.

The number of the part of the plasticizer added (except for the halogen-terminated sulfur-containing polymer of the present invention) is determined depending on the design of the strength and elongation of the cured material, and also the viscosity before curing, and is preferably 1 to 100 parts by weight, based on 100 parts by weight of the liquid polysulfide polymer. When exceeding 100 parts by weight, non-reactive liquid components may increase, and the hardness may not be maintained. The part of the plasticizer added is more preferably 1 to 50 parts by weight and further more preferably 1 to 30 parts by weight.

The curable composition may contain, for the purpose of improving economic efficiency, workability when preparing a composition and physical properties after curing, at least one each of fillers, multifunctional crosslinking agents, curing accelerators, adhesion promoters, UV absorbers, antioxidants, tackifiers, rubber and elastomer, flowable additives, fungicides, corrosion inhibitors, pigments, masking agents or additives having different effects, as necessary.

The filler includes hollow fillers such as inorganic fillers such as calcium carbonate, aluminum oxide, aluminum hydroxide, silica, molecular sieves, silicates and sulfates, light weight polymer fillers such as carbon black, polyamide and polyethylene, thermoplastic balloons (thermal expansion microcapsules) such as silica, acrylonitrile, methacrylonitrile and vinylidene chloride, thermosetting balloons such as phenol and epoxy, and inorganic balloons such as shirasu, fly ash, glass and alumina, and the like. Two or more kinds of the fillers may be used, and the fillers on which surface is treated with a fatty acid, a resin acid, a surfactant, a silane coupling agent, paraffin, a catalyst or the like may be used. Calcium carbonate is preferably heavy calcium carbonate and colloidal calcium carbonate.

The multifunctional crosslinking agent includes trimethylolpropane trimercaptopropionate, trimethylolpropane trimercaptoacetate, pentaerythritol-tetrakis-3-mercaptopropionate, and the like. Two or more kinds of the multifunctional crosslinking agents may be used.

The curing accelerator includes vulcanization accelerators such as aldehyde-ammonia and aldehyde-amine, thiourea, guanidine, thiazol, sulfenamide, thiuram, dithiocarbamate, and xanthogenate. Specifically, the curing accelerator includes tris(dimethylaminomethyl)phenol, diphenylguanidine, tetramethylthiuram disulfide, tetraethylthiuram disulfide, tetrabutylthiuram disulfide, hexamethylenetetramine, and the like. Two or more kinds of the curing accelerators may be used.

The adhesion promoter includes silane coupling agents containing a hydrolyzable silyl group and a reactive organic functional group. Specifically, the adhesion promoter includes vinyltrimethoxysilane, vinyltriethoxysilane, 2-(3,4-epoxycyclohexyl)ethyltrimethoxysilane, 3-glycidoxypropyltrimethoxysilane, 3-glycidoxypropylmethyldiethoxysilane, 3-glycidoxypropyltriethoxysilane, p-styryltrimethoxysilane, 3-methacryloxypropylmethyldimethoxysilane, 3-methacryloxypropyltrimethoxysilane, 3-methacryloxypropylmethyldiethoxysilane, 3-methacryloxypropyltriethoxysilane, 3-acryloxypropyltrimethoxysilane, N-2 (aminoethyl)-3-aminopropylmethyldimethoxysilane, N-2 (aminoethyl)-3-aminopropyltrimethoxysilane, N-2 (aminoethyl)-3-aminopropyltriethoxysilane, 3-aminopropyltrimethoxysilane, 3-aminopropyltriethoxysilane, 3-triethoxysilyl-N-(1,3-dimethyl-butylidene)propylamine, N-phenyl-3-aminopropyltrimethoxysilane, 3-mercaptopropylmethyldimethoxysilane, 3-mercaptopropyltrimethoxysilane, bis(triethoxysilylpropyl)tetrasulfide, and the like. In addition, a terminal trimethoxysilane modified polysulfide polymer synthesized by reacting a polysulfide polymer "Thiokol LP-3" with 3-glydoxypropyltrimethoxysilane can be also used as a silane coupling agent. Two or more kinds of the silane coupling agents may be used.

The UV absorber includes benzophenones, benzotriazoles, phenyl salicylates, triazines, nickel salts, and nickel complex salts. Specifically, the UV absorber includes 2-(2-hydroxy-5-methylphenyl)benzotriazole, 2-[2-hydroxy-3(3,4,5,6-tetrahydrophthalimidomethyl)-5-methylphenyl]benzotriazole, 2-(2-hydroxy-3-t-butyl-5-methylphenyl)-5-chlorobenzotriazole, 2-(2-hydroxy-4-octylphenyl)benzotriazole, 2-(2-hydroxy-3,5-t-butylphenyl)benzotriazole, 2-(2-hydroxy-3,5-t-butylphenyl)-5-chlorobenzotriazole, 2-(2-hydroxy-5-t-octylphenyl)benzotriazole, 2-(2-hydroxy-3,5-di-t-amylphenyl)benzotriazole, nickel dibutyl dithiocarbamate, [2,2'-thiobis(4-t-octylphenolate)]-2-ethylhexylamine-nickel, and the like.

Examples of the antioxidant include amine antioxidants, phenolic antioxidants, phosphite antioxidants, and thioether antioxidants. Specifically, the antioxidant includes 1,3,5-tris[[3,5-bis(1,1-dimethylethyl)-4-hydroxyphenyl]methyl]-1,3,5-triazine-2,4,6(1H,3H,5H)-trione, 1,1,3-tris(5-tert-butyl-4-hydroxy-2-methylphenyl)butane, 1,1-bis(4-hydroxy-2-methyl-5-tert-butylphenyl)butane, 2,2-bis[[[3-(3,5-di-tert-butyl-4-hydroxyphenyl)propionyl]oxy]methyl]propane-1,3-diol 1,3-bis[3-(3,5-di-tert-butyl-4-hydroxyphenyl) propionate], bis(3-tert-butyl-4-hydroxy-5-methylbenzenepropanoic acid)ethylenebis(oxyethylene), 4,4',4"-[(2,4,6-trimethylbenzene-1,3,5-triyl)tris(methylene)]tris(2,6-di-tert-butylphenol), and the like.

The tackifier includes phenol resins, coumarone-indene resins, coumarone resins, naphthenic oils, rosin, rosin esters, hydrogenated rosin derivatives, terpene resins, modified terpene resins, terpene-phenolic resins, hydrogenated terpene resins, α-pinene resins, alkylphenol-acetylene resins, alkylphenol-formaldehyde resins, styrene resins, $C_6$ petroleum resins, $C_9$ petroleum resins, alicyclic petroleum resins, $C_6/C_9$ copolymerized petroleum resins, xylene-formaldehyde resins, and the like.

The rubber and elastomer include natural rubbers, polybutadiene rubbers, acrylic rubbers, polyisoprene rubbers, styrene-butadiene rubbers, acrylonitrile-butadiene rubbers, chloroprene rubbers, olefinic elastomers, styrenic elastomers, vinyl chloride elastomers, polyester elastomers, polyamide elastomers, polyurethane elastomers, polysiloxane elastomers, and the like.

The flowable additive includes fumed silica, colloidal hydrated aluminum silicate/organic complex, saturated fatty acid (salt) compounds, precipitated calcium carbonate treated with a saturated fatty acid (salt) compound, and the like. The saturated fatty acid (salt) compound includes hexanoic acid, octanoic acid, decanoic acid, lauric acid, myristic acid, palmitic acid, stearic acid, succinic acid, glutaric acid, adipic acid, pimelic acid, suberic acid, azelaic acid, sebacic acid, and sodium, calcium, and magnesium salts thereof, and the like.

The curable composition has excellent oil resistance, weather resistance, water tightness and gas tightness, and also good in adhesion, thus can be used for a sealant, adhesive and paint, and the like.

The halogen-terminated sulfur-containing polymer can easily thiolate the terminal by reacting sodium hydrosulfide or the like, and is thus also effective as an intermediate when manufacturing a thiol group-terminated polysulfide polymer. Furthermore, the halogen-terminated sulfur-containing polymer can easily synthesize a compound other than compounds having a thiol terminal by adding a compound that reacts with a halogen.

EXAMPLES

Hereinbelow, our polymers and methods will be described in further detail by way of the following examples.

GPC Analysis and Determination of Number Average Molecular Weight (Mn)

Columns of TSKgel G3000HXL, TSKgel G2000HXL and TSKgel G1000HXL connected in series were used, and detectors of MODEL 504R RI Detector manufactured by GL Sciences Inc. and L-4000 UV Detector manufactured by Hitachi, Ltd. were used. Using THF with a flow rate of 1.0 ml/min as a mobile phase, the determination was performed at a column temperature of 40° C. PPG was used for the conversion of the molecular weight.

Calculation of Average of r and Average of n

A sample was burned in an electric furnace, and the total sulfur content was obtained by analyzing the sample according to a predetermined sulfur analysis method, using chlorine/sulfur analyzer TOX-100 manufactured by Mitsubishi Chemical Corporation that determines the amount of the produced sulfur dioxide by potentiometric titration to calculate the sulfur concentration in the sample. Based on the total sulfur content and the number average molecular weight of Mn, the average of r and the average of n were calculated.

For example, in Example 1, the halogen-terminated sulfur-containing polymer was produced from bis(2-chloroethyl)formal and 1,2,3-trichloropropane. The initial molar ratio of bis(2-chloroethyl)formal and 1,2,3-trichloropropane was 98:2. The terminal halogen was a chlorine atom. Thus, when the halogen-terminated sulfur-containing polymer was Cl—(Y—$S_r$)$_n$—Y—Cl the averages were calculated supposing that the structure of Y was composed of $C_2H_4OCH_2OC_2H_4$ and $CH_2CHCH_2$ in a molar ratio of 98:2.

Determination of Chlorine Content

A sample was burned in an electric furnace, and the chlorine content was analyzed according to a predetermined chlorine analysis method, using chlorine/sulfur analyzer TOX-100 manufactured by Mitsubishi Chemical Corporation that determines the amount of the produced hydrogen chloride by potentiometric titration to calculate the chlorine concentration in the sample.

Example 1

In a 2 L-buffled separable flask, 419.3 g of sodium monosulfide (purity of 59.4%), 830 g of water, 4.6 g of a 50 wt % aqueous tetrabutylammonium chloride solution, 640 g of bis(2-chloroethyl)formal and 11.0 g of 1,2,3-trichloropropane were reacted at 80° C. Furthermore, the substances were reacted at 100° C. for 1 hour, then water in the upper layer was removed by decantation, and dehydrated and dried with an evaporator. 3% of a filter aid was added to the resulting crude chloro terminal polymer, and the mixture was stirred, and purified by a pressure filter, to obtain about 520 g of a clear liquid. The resulting polymer had a Mn by GPC of 762, an average of sulfur r of 1.0, and an average of n of 4, and a Cl content of 6.5%.

Example 2

In a 2 L-buffled separable flask, 409.8 g of sodium monosulfide (purity of 59.4%), 86.3 g of sodium hydrosulfide (purity of 71.7%), 69.9 g of sulfur, 830 g of water, 4.6 g of a 50 wt % aqueous tetrabutylammonium chloride solution, 640 g of bis(2-chloroethyl)formal and 11.0 g of 1,2,3-trichloropropane were reacted at 80° C. Furthermore, the substances were reacted at 100° C. for 1 hour, then water in the upper layer was removed by decantation, and dehydrated and dried with an evaporator. 3% of a filter aid was added to the resulting crude chloro terminal polymer, and the mixture was stirred, and purified by a pressure filter, to obtain about 520 g of a pale yellow clear liquid. The resulting polymer had a Mn by GPC of 714, an average of sulfur r of 1.6, and an average of n of 3, and a Cl content of 6.7%.

Example 3

In a 2 L-buffled separable flask, 405.8 g of sodium monosulfide (purity of 59.4%), 830 g of water, 4.6 g of a 50 wt % aqueous tetrabutylammonium chloride solution and 640 g of bis(2-chloroethyl)formal were reacted at 80° C. Thereafter, the substances were reacted at 100° C. for 4 hours. After completion of the reaction, water in the upper layer was removed by decantation, and dehydrated and dried with an evaporator. 3% of a filter aid was added to the resulting crude chloro terminal polymer, and the mixture was stirred, and purified by a pressure filter, to obtain about 520 g of a clear liquid. The resulting polymer had a Mn by GPC of 690, an average of sulfur r of 2.0, and an average of n of 3, and a Cl content of 6.6%.

Example 4

In a 2 L-buffled separable flask, 462.3 g of sodium monosulfide (purity of 59.4%), 830 g of water, 4.6 g of a 50 wt % aqueous tetrabutylammonium chloride solution and 640 g of bis(2-chloroethyl)formal were reacted at 80° C. Thereafter, the substances were reacted at 100° C. for 4 hours. After completion of the reaction, water in the upper layer was removed by decantation, and dehydrated and dried with an evaporator. 3% of a filter aid was added to the resulting crude chloro terminal polymer, and the mixture was stirred, and purified by a pressure filter, to obtain about 520 g of a clear liquid. The resulting polymer had a Mn by GPC of 1299, an average of sulfur r of 1.0, and an average of n of 8, and a Cl content of 2.4%.

Example 5

In a 2 L-buffled separable flask, 462.3 g of sodium monosulfide (purity of 59.4%), 830 g of water, 6.0 g of a 50 wt % aqueous tetrabutylammonium bromide solution and 640 g of bis(2-chloroethyl)formal were reacted at 80° C. Thereafter, the substances were reacted at 100° C. for 4 hours. After completion of the reaction, water in the upper layer was removed by decantation, and dehydrated and dried with an evaporator. 3% of a filter aid was added to the resulting crude chloro terminal polymer, and the mixture was stirred, and purified by a pressure filter, to obtain about 520 g of a clear liquid. The resulting polymer had a Mn by GPC of 1256, an average of sulfur r of 1.0, and an average of n of 8, and a Cl content of 2.4%.

In Table 1, physical properties of Examples 1 to 5 and plasticizers, butyl benzyl phthalate (manufactured by DAIHACHI CHEMICAL INDUSTRY CO., LTD.), dipropylene glycol dibenzoate (Benzoflex 9-88, manufactured by EASTMAN CHEMICAL COMPANY), chlorinated paraffin (Toyoparax 150, manufactured by TOSOH CORPORATION), DOP (dioctyl phthalate, manufactured by DAIHACHI CHEMICAL INDUSTRY CO., LTD.) and DNP (diisononyl phthalate, manufactured by DAIHACHI CHEMICAL INDUSTRY CO., LTD.) used in the sealants are shown.

TABLE 1

| | Compatibility with LP | Compatibility with P-3 | Average Sulfur Content r | Chlorine Content (%) | Number Average Molecular Weight | Viscosity (Pa·s) | Glass-Transition Temperature (°C.) | 50% Decomposition Temperature (°C.) | Heating Loss (%) |
|---|---|---|---|---|---|---|---|---|---|
| Polymer of Example 1 | Compatible | Compatible | 1.0 | 6.5 | 762 | 0.6 | −76 | 329 | 0.4 |
| Polymer of Example 2 | Compatible | Compatible | 1.6 | 6.7 | 714 | 1.2 | −68 | 314 | 0.7 |
| Polymer of Example 3 | Compatible | Compatible | 2.0 | 6.6 | 690 | 1.3 | −68 | 310 | 0.7 |
| Polymer of Example 4 | Compatible | Compatible | 1.0 | 2.4 | 1299 | 4.0 | −72 | 342 | 0.6 |
| Polymer of Example 5 | Compatible | Compatible | 1.0 | 2.4 | 1256 | 3.9 | −72 | 340 | 0.5 |
| BBP (Butyl Benzyl Phthalate) | Compatible | Compatible | — | 0 | 202 | 0.04 | −68 | 282 | 0.4 |
| Dipropylene Glycol Dibenzoate | Compatible | Compatible | — | 0 | 263 | 0.1 | −48 | 289 | 8.9 |
| Chlorinated Paraffin (Toyoparax 150) | Compatible | Compatible | — | 50 | 293 | 1.2 | −51 | 294 | 2.3 |
| DOP (Dioctyl Phthalate) | Incompatible (Two-Phase Separation) | Incompatible (Two-Phase Separation) | — | 0 | 353 | 0.06 | −80 or less | 288 | 1.4 |
| DINP (Diisononyl Phthalate) | Incompatible (Two-Phase Separation) | Incompatible (Two-Phase Separation) | — | 0 | 400 | 0.06 | −80 or less | 305 | 3.8 |

In Table 1, the compatibility with LP was visually confirmed after mixing polysulfide polymer LP-23 manufactured by Toray Fine Chemicals Co., Ltd. and a plasticizer in a weight ratio of 1:1 and leaving the mixture at room temperature for 10 minutes.

Compatibility with P-3 was visually confirmed after mixing polythioether polymer (Permapol P-3) manufactured by PPG Industries and a plasticizer in a weight ratio of 1:1 and leaving the mixture at room temperature for 10 minutes.

Viscosity was determined by a sample viscosity at 25° C. using viscometer U-EII manufactured by Toki Sangyo Co., Ltd. The glass-transition temperature was obtained from a DSC curve when about 10 mg of sample was heated at a constant rate of 10° C./min from −90° C. to 10° C. in a nitrogen atmosphere, using differential scanning calorimeter DSC Q10 manufactured by TA Instruments, Inc.

The 50% decomposition temperature was defined as a temperature at which the weight is 50% of the initial weight, in the TGA curve when about 30 mg of sample was heated at a constant rate of 10° C./min from room temperature to 500° C. in a nitrogen atmosphere, using thermogravimetric analyzer TGA Q50 manufactured by TA Instruments, Inc.

Heating loss is a weight loss ratio at 80° C. after 2 W. About 4 g of sample was accurately weighed on a watch glass, put in a thermostat at 80° C., and cured for 2 weeks. The sample returned to room temperature was weighed, and the ratio of the weight change relative to the initial weight was defined as the weight loss ratio.

Based on Table 1, DOP (dioctyl phthalate) and DNP (diisononyl phthalate) have poor compatibility with a polysulfide polymer and a polythioether polymer, and cannot be used as a plasticizer. Dipropylene glycol dibenzoate (Benzoflex 9-88) and chlorinated paraffin (Toyoparax 150) have large heating loss. BBP (butyl benzyl phthalate) is listed as a safety hazardous material in Europe, and the future usage is possibly restricted.

The polymers of Examples 1 to 5 do not fall under the such safety regulations. The polymers of Examples 1 to 5 have high compatibility with a polysulfide polymer and a polythioether polymer, and are preferable as a plasticizer. In addition, the polymers of Examples 1 to 5 have further lower glass-transition temperature than that of BBP, and have high 50% decomposition temperature, and thus have high plasticizing efficiency and thermal resistance. Specifically, the lower the average of sulfur r, the lower the glass-transition temperature, and the higher the 50% weight loss temperature.

Example 6

First, a polysulfide polymer (LP-23, manufactured by Toray Fine Chemicals Co., Ltd.), the polymer of Example 1 and SRF carbon as base compound were mixed using a roller, and manganese dioxide (Type-FA (manufactured by HONEYWELL INTERNATIONAL Inc.)), BBP (butyl benzyl phthalate) and tetrabutylthiuram disulfide (NOCCELER TBT-N, manufactured by OUCHI SHINKO CHEMICAL INDUSTRIAL CO., LTD.) as curing agent were mixed using a roller. Next, the base compound and the curing agent were well kneaded by hand mixing. The mixing ratio of the polysulfide polymer (LP-23), the polymer of Example 1, SRF carbon, manganese dioxide, BBP (butyl benzyl phthalate) and tetrabutylthiuram disulfide was as described below.

| | |
|---|---|
| LP-23 (manufactured by Toray Fine Chemicals Co., Ltd.) | 100 parts by weight |
| Polymer of Example 1 | 60 parts by weight |
| SRF carbon | 35 parts by weight |
| Manganese dioxide (Type-FA) | 10 parts by weight |
| BBP (butyl benzyl phthalate) | 10 parts by weight |
| Tetrabutylthiuram disulfide | 0.5 parts by weight |

The mixture was heated and cured at 70° C. for 2 hours, and a sheet-like cured composition with a thickness of 2 mm was prepared, then the resulting sheet was evaluated. The hardness was measured by type A durometer according to JIS K6253. Dumbbell tensile properties were determined by performing a tensile test at 500 mm/min and a gauge length of 20 mm, using dumbbell No. 5 according to JIS K6251. The glass-transition temperature was obtained from a DSC curve when about 10 mg of sample was heated at a constant rate of 10° C./min from −90° C. to 10° C. in a nitrogen atmosphere, using differential scanning calorimeter DSC Q10 manufactured by TA Instruments, Inc. These values are shown in Table 2.

Example 7

The same procedures were carried out as in Example 6, using the polymer of Example 4 in the base compound, in place of the polymer of Example 1. The mixture of the base compound and the curing agent was heated and cured at 70° C. for 2 hours, and a sheet-like cured composition with a thickness of 2 mm was prepared, then the resulting sheet was evaluated. The measurement result is shown in Table 2.

Comparative Example 1

The same procedures were carried out as in Example 6, mixing LP-23 and SRF carbon as base compound using a roller. The mixture of the base compound and the curing agent was heated and cured at 70° C. for 2 hours, and a sheet-like cured composition with a thickness of 2 mm was prepared, then the resulting sheet was evaluated. Comparative Example 1 does not contain the polymer of Example 1 in the base compound. The measurement result is shown in Table 2.

Comparative Example 2

The same procedures were carried out as in Example 6, using BBP (butyl benzyl phthalate, manufactured by DAIHACHI CHEMICAL INDUSTRY CO., LTD.) in the base compound, in place of the polymer of Example 1. The mixture of the base compound and the curing agent was heated and cured at 70° C. for 2 hours, and a sheet-like cured composition with a thickness of 2 mm was prepared, then the resulting sheet was evaluated. The measurement result is shown in Table 2.

Comparative Example 3

The same procedures were carried out as in Example 6, using dipropylene glycol dibenzoate (Benzoflex 9-88, manufactured by EASTMAN CHEMICAL COMPANY) in the base compound, in place of the polymer of Example 1. The mixture of the base compound and the curing agent was heated and cured at 70° C. for 2 hours, and a sheet-like cured composition with a thickness of 2 mm was prepared, then the resulting sheet was evaluated. The measurement result is shown in Table 2.

Comparative Example 4

The same procedures were carried out as in Example 6, using chlorinated paraffin (Toyoparax 150, manufactured by TOSOH CORPORATION) in the base compound, in place of the polymer of Example 1. The mixture of the base compound and the curing agent was heated and cured at 70° C. for 2 hours, and a sheet-like cured composition with a thickness of 2 mm was prepared, then the resulting sheet was evaluated. The measurement result is shown in Table 2.

TABLE 2

|  | Example 6 | Example 7 | Comparative Example 1 | Comparative Example 2 | Comparative Example 3 | Comparative Example 4 |
|---|---|---|---|---|---|---|
| LP-23 | 100 | 100 | 100 | 100 | 100 | 100 |
| Polymer of Example 1 | 60 | — | — | — | — | — |
| Polymer of Example 4 | — | 60 | — | — | — | — |
| BBP (Butyl Benzyl Phthalate) | — | — | — | 60 | — | — |
| Dipropylene Glycol Dibenzoate (Benzoflex 9-88) | — | — | — | — | 60 | — |
| Chlorinated Paraffin (Toyoparax 150) | — | — | — | — | — | 60 |
| SRF Carbon | 35 | 35 | 35 | 35 | 35 | 35 |
| Manganese Dioxide | 10 | 10 | 10 | 10 | 10 | 10 |
| BBP (Butyl Benzyl Phthalate) | 10 | 10 | 10 | 10 | 10 | 10 |
| Tetrabutylthiuram Disulfide | 0.5 | 0.5 | 0.5 | 0.5 | 0.5 | 0.5 |
| Hardness (Shore A) | 10 | 11 | 53 | 19 | 20 | 24 |
| Tensile Stress at 100% Elongation (N/mm$^2$) | 0.15 | 0.16 | 1.54 | 0.30 | 0.33 | 0.39 |
| Tensile Strength (N/mm$^2$) | 0.36 | 0.48 | 3.5 | 0.48 | 0.53 | 0.93 |
| Elongation at Break % | 379 | 470 | 295 | 256 | 257 | 268 |
| Glass-Transition Temperature (° C.) | −67 | −61 | −57 | −61 | −56 | −55 |
| 20% Decomposition Temperature (° C.) | 277 | 284 | 274 | 246 | 250 | 252 |

In Table 2, the tensile stress at 100% elongation on the dumbbell tensile measurement, the tensile strength on the dumbbell tensile measurement, the elongation at break on the dumbbell tensile measurement, the glass-transition temperature and the 20% decomposition temperature were summarized. The 20% decomposition temperature refers to a temperature at which the weight is 80% of the initial weight in the TGA curve when heated at a constant rate of 10° C./min in a nitrogen atmosphere by TGA.

Based on Table 2, in the cured compositions of Examples 6 and 7, decrease in hardness, decrease in dumbbell tensile properties and decrease in the glass-transition temperature were seen, as compared to Comparative Example 1 to which a plasticizer was not added, thus increases in plasticizing effects and low-temperature flexing was confirmed. The 20% weight loss temperature was raised, thus improvement in heat resistance was also confirmed. In addition, in the cured compositions of Examples 6 and 7, the glass-transition temperature was further decreased and the 20% weight loss temperature was also raised, more than other plasticizer-added compositions of Comparative Examples 2 to 4, thus improvements in low-temperature flexing and heat resistance was also confirmed.

INDUSTRIAL APPLICABILITY

The halogen-terminated sulfur-containing polymer is industrially very useful as a plasticizer of a polysulfide poly-

The invention claimed is:

1. A halogen-terminated sulfur-containing polymer represented by:

$$X-(R-S_r)_n-R-X;$$

wherein R is an ether bond-containing alkyl group having 3 to 26 carbon atoms comprising —O—CH$_2$—O— bond-containing alkyl group, X is a halogen atom, n is an integer of 1 to 200, and r has an average of 1 or more and less than 2, and a number average molecular weight of 500-10,000.

2. The halogen-terminated sulfur-containing polymer according to claim 1, wherein R is an ether bond-containing alkyl group having 3 to 16 carbon atoms containing a branched alkylene group.

3. The halogen-terminated sulfur-containing polymer according to claim 1, wherein R is an alkyl group containing —C$_2$H$_4$—O—CH$_2$—O—C$_2$H$_4$— in an amount of 50 mol % or more.

4. The halogen-terminated sulfur-containing polymer according to claim 1, wherein R further contains a branched alkylene group represented by

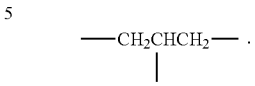

5. The halogen-terminated sulfur-containing polymer according to claim 1, wherein X is a chlorine atom.

6. A curable composition comprising the halogen-terminated sulfur-containing polymer as defined in claim 1, a polysulfide polymer, and a curing agent.

7. A curable composition comprising the halogen-terminated sulfur-containing polymer as defined in claim 2, a polysulfide polymer, and a curing agent.

8. A curable composition comprising the halogen-terminated sulfur-containing polymer as defined in claim 3, a polysulfide polymer, and a curing agent.

9. A curable composition comprising the halogen-terminated sulfur-containing polymer as defined in claim 4, a polysulfide polymer, and a curing agent.

10. A curable composition comprising the halogen-terminated sulfur-containing polymer as defined in claim 5, a polysulfide polymer, and a curing agent.

* * * * *